United States Patent [19]

Bonner

[11] Patent Number: 5,609,621
[45] Date of Patent: Mar. 11, 1997

[54] RIGHT VENTRICULAR OUTFLOW TRACT DEFIBRILLATION LEAD

[75] Inventor: Matthew D. Bonner, Plymouth, Minn.

[73] Assignee: Medtronic, Inc., Minneapolis, Minn.

[21] Appl. No.: 511,200

[22] Filed: Aug. 4, 1995

[51] Int. Cl.$^6$ .................................................. A61N 1/39
[52] U.S. Cl. ............................................... 607/122
[58] Field of Search .................. 607/122, 123, 607/127, 126

[56] References Cited

U.S. PATENT DOCUMENTS

| | | |
|---|---|---|
| 3,729,008 | 4/1973 | Berkovits . |
| 4,106,512 | 8/1978 | Bisping . |
| 4,161,952 | 7/1979 | Kinney . |
| 4,355,646 | 10/1982 | Kallok . |
| 4,402,330 | 9/1983 | Lindemans . |
| 4,414,986 | 11/1983 | Dickhudt . |
| 4,481,953 | 11/1984 | Gold . |
| 4,708,145 | 11/1987 | Tacker . |
| 4,934,049 | 6/1990 | Kiekhafer . |
| 4,951,687 | 8/1990 | Ufford . |
| 4,953,551 | 9/1990 | Mehra . |
| 4,998,975 | 3/1991 | Cohen . |
| 5,007,436 | 4/1991 | Smits . |
| 5,010,894 | 4/1991 | Edhag . |
| 5,042,143 | 8/1991 | Holleman . |
| 5,044,374 | 9/1991 | Lindemans . |
| 5,050,601 | 9/1991 | Kupersmith . |
| 5,099,838 | 3/1992 | Bardy . |
| 5,107,834 | 4/1992 | Ideker . |
| 5,111,811 | 5/1992 | Smits . |
| 5,133,365 | 7/1992 | Heil, Jr. . |
| 5,144,960 | 9/1992 | Mehra . |
| 5,165,403 | 11/1992 | Mehra . |
| 5,170,802 | 12/1992 | Mehra . |
| 5,174,288 | 12/1992 | Bardy . |
| 5,433,729 | 7/1995 | Adams et al. ............... 607/5 |

*Primary Examiner*—William E. Kamm
*Assistant Examiner*—Scott M. Getzow
*Attorney, Agent, or Firm*—Reed A. Duthler; Harold R. Patton

[57] ABSTRACT

A cardioversion/defibrillation lead and method of implantation thereof for location in a human heart of the type comprising an elongated lead body having proximal and distal end sections and having a looped intermediate section. The proximal and distal end sections of the lead have generally straight configurations, and the intermediate section is constructed such that when the distal section is located at the apex of the right ventricle of the heart, the loop of the intermediate section is located in the outflow tract of the heart. One or more elongated defibrillation electrode(s) extends along the intermediate section of the lead body.

16 Claims, 3 Drawing Sheets

RIGHT VENTRICULAR OUTFLOW TRACT DEFIBRILLATION LEAD

FIELD OF THE INVENTION

The present invention relates to medical stimulators and leads generally, and more particularly to implantable defibrillators and defibrillation leads.

BACKGROUND OF THE INVENTION

Currently available implantable ventricular defibrillators, including the multi-programmable, pacemaker/cardioverter/defibrillator, typically employ epicardial or subcutaneous patch electrodes, alone, or in conjunction with one or more endocardial leads with one or more electrodes disposed within a heart chamber or blood vessel. Multi-lead and multi-electrode atrial and/or ventricular defibrillation systems are widely disclosed, as exemplified in U.S. Pat. Nos. 4,708,145 to Tacker, et al., 4,998,975 to Cohen et al., 5,007,436 to Smits, 5,099,838 to Bardy, 5,107,834 to Ideker et al, 5,111,811 to Smits, 5,165,403 to Mehra, and 5,174,288 to Bardy et al. Ventricular defibrillation is typically effected with at least one electrode disposed within the right ventricle and one or more electrodes disposed outside the right ventricle. Many versions of right ventricular defibrillation electrodes have been disclosed in the above listed patents and in further single endocardial lead systems as shown, for example, in further U.S. Pat. Nos. 4,481,953 to Gold et al., 4,161,952 to Kinney, et al., 4,934,049 to Kiekhafer et al., 5,010,894 to Edhag, 5,042,143 to Holleman, et al., 5,050,601 to Kupersmith et al., 5,133,365 to Heil, Jr. et al., and 5,144,960 to Mehra et al.

The positioning of the right ventricular (RV) lead electrode in proximity to the septum of the heart is considered to be desirable. In the above-referenced '975, '436, '811, '834 and '894 patents, U-shaped RV defibrillation leads are described and depicted which have at least a distal portion of the elongated defibrillation electrode shaped to bear against the septum. A U-shaped loop biased into the apex of the right ventricle is relied on to provide the force to press the distal portion back proximally along the septum. These RV leads either have a single or multiple defibrillation electrodes spaced along the lead body. In the '834 patent, the distal end of the lead bears a separate electrode that is intended to be directed into the outflow tract through the tri-cuspid valve while more proximally located RV electrodes and superior vena cava/right atrial (SVC/RA) electrodes are positioned in the right ventricle and the right atrium or superior vena cava, respectively.

In leads of this type, it is necessary to employ a separate pace/sense RV electrode bearing lead that is wedged deep into the apex of the right ventricle or to rely on a ring shaped electrode as shown in the '834 patent. In the latter case, it is not possible to obtain the deep apical penetration of the pace/sense RV ring electrode, and pacing is compromised by the poor contact with myocardial cells. In the '894 and '975 patents, additional RV lead structures are disclosed that employ active or passive fixations mechanisms for fixing the RV pace sense electrodes on the lead bodies. A pair of RV defibrillation electrodes are formed on bifurcations of the lead body or in free legs that extend back from the point of attachment in the apex of the right ventricle. These configurations are unduly complex and difficult to fabricate.

In these configurations and in the above-referenced '365 patent, attempts are made to provide at least some contact of the RV defibrillation electrodes along the septum in order to attain a distribution of defibrillation energy therein. Further approaches to distributing the defibrillation energy along and into the septum of the right ventricle are also disclosed in the above-referenced '960 and '601 patents. The RV leads disclosed therein have commonly connected branch RV defibrillation electrodes extending laterally from an intermediate or proximal point along the primary, straight RV defibrillation electrode. In the '960 patent, the branch defibrillation electrode is extended toward the outflow tract.

Despite these improvements, a problem of maintaining good contact of the elongated RV defibrillation electrode along the septum with an RV defibrillation lead that is simple to fabricate and simple to insert and position remains unsatisfied.

SUMMARY OF THE INVENTION

The present invention is directed toward the provision of an endocardial defibrillation lead particularly optimized for use in conjunction with one or more epicardial patch or subcutaneous patch electrodes or a subcutaneous electrode formed as part of or all of the outer housing or "can" of an implantable defibrillator. The electrode may also possibly be used in conjunction with other endocardial electrodes, such as SVC/RA electrodes or coronary sinus (CS) electrodes.

The lead is provided with an elongated body, including a elongated, generally straight proximal section, a distal section carrying pacing and sensing electrodes and an intermediate $\Omega$-shaped electrode bearing section comprising a generally straight, first leg portion extending from the proximal section of the lead body, a first loop portion and a second generally straight leg portion extending from the loop portion to the distal section of the lead body. The $\Omega$-shaped section preferably diverges from the axis of the proximal section of the lead body, such that the junction of the first leg portion with the proximal lead section defines a second loop, such that the first leg portion extends back toward the proximal end of the lead and the second leg portion extends from the first loop portion towards the distal end of the lead. The first and second loop portions are preferably, but not necessarily coplanar. The lead is preferably sized so that in use, the lead may be inserted into the right ventricle such that the distal straight end is located at the ventricular apex and the first loop portion of the $\Omega$-shaped electrode bearing section is located in the outflow tract of the right ventricle. One of the two generally straight leg portions is thereby urged toward and extends along the septum. The electrode may take the form of an elongated, biocompatible, conductive metal coiled wire, exposed to the exterior of the lead body. Alternatively, a plurality of coil electrode sections or a series of closely spaced ring electrodes may be employed.

The lead design allows for an endocardial cardioversion/defibrillation electrode which is widely distributed within the right ventricle, providing for a substantial increase in electrode surface area and distributing the surface area more widely, with respect to the left ventricle. This improvement in the lead and electrode configuration is believed to be helpful in improving the current distribution between the RV electrode and the associated electrode or electrodes. In its preferred embodiment, the RV lead of the present invention is used with only a single additional lead bearing electrode, e.g. a subcutaneously implanted can electrode, thus simplifying the implant procedure required to complete the implantation of the system.

The distal, section of the RV lead is provided with a bipolar pace/sense electrode pair, e.g. an endocardial screw-in electrode similar to that used in prior art endocardial screw-in pacing leads. This electrode serves to anchor and locate both the pace/sense electrode pair and the defibrillation electrode on the RV lead. The Ω-shaped section of the RV lead is maintained in the outflow tract solely as a result of its attachment to the remainder of the lead body and its curved configuration. This approach is believed to be substantially superior to the approach illustrated in the Smits patents cited above, which attempted to accomplish an increase in surface area and an improvement in electrode surface distribution within the right ventricle by means of a U-shaped electrode, having the apex of the "U" shaped curve located in the ventricular apex and the pacing and sensing electrodes located at the distal end of the U-shaped portion of the lead body.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

Figure 1:
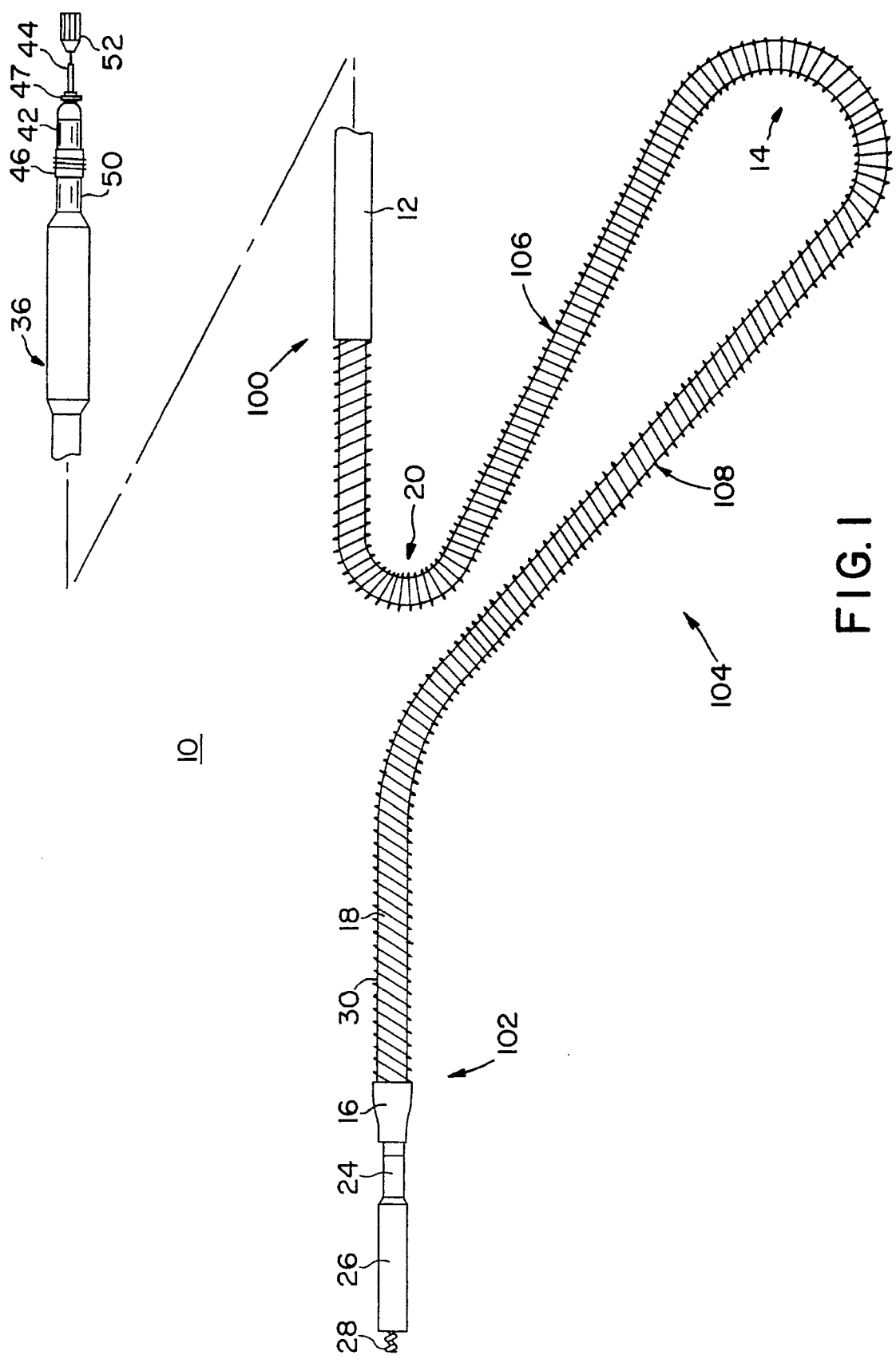
FIG. 1 is a plan view of one embodiment of the Ω-shaped, RV defibrillation lead according to the present invention.

FIG. 1 illustrates a preferred embodiment of the RV defibrillation lead 10 according to the present invention. The straight distal end of the lead 10 is provided with a pacing and sensing electrode assembly including an extendable helix, pace/sense electrode 28, mounted retractably within an insulative electrode head 26, and a ring shaped pace/sense electrode 24 forming a pace/sense electrode pair. A transitional insulative sleeve 16 overlaps and stabilizes the distal end of the elongated, exposed coiled wire defibrillation electrode 30 which terminates just proximal of the ring-shaped pace/sense electrode 24.

The lead body is configured to include an elongated, generally straight proximal section 100, a distal section 102 carrying the pacing and sensing electrodes 28 and 24 and an intermediate Ω-shaped electrode bearing section 104 comprising a generally straight, first leg portion extending from the proximal section 100 of the lead body, a first loop portion 14 and a second generally straight leg portion 108 extending from the first loop portion 14 to the distal section 102 of the lead body. The Ω-shaped section preferably diverges from the axis of the proximal section of the lead body, such that the junction of the first leg portion with the distal end of proximal lead section 100 defines a second loop 20, such that the first leg portion 106 extends back toward the proximal end of the lead and the second leg portion 108 extends from the first loop portion towards the distal end of the lead. Sheath 12 contains three concentric or co-axial coiled wire conductors, separated from one another by tubular insulative sheaths and having a single interior lumen. This tripolar, co-axial arrangement is illustrated in more detail in U.S. Pat. No. 4,355,646, issued to Kallok et al. incorporated herein by reference in its entirety. As set forth in the '646 patent, the insulative sheaths employed in the present lead may be made of an implantable polyurethane. However, in some embodiments, the sheaths may be made of silicone rubber or other implantable, flexible plastic. The conductor coils may be made of Drawn Brazed Strand wire (DBS), previously used in cardiac pacing leads or may be an other implantable metal such as MP35N alloy, also commonly used in pacing leads.

Figure 2:
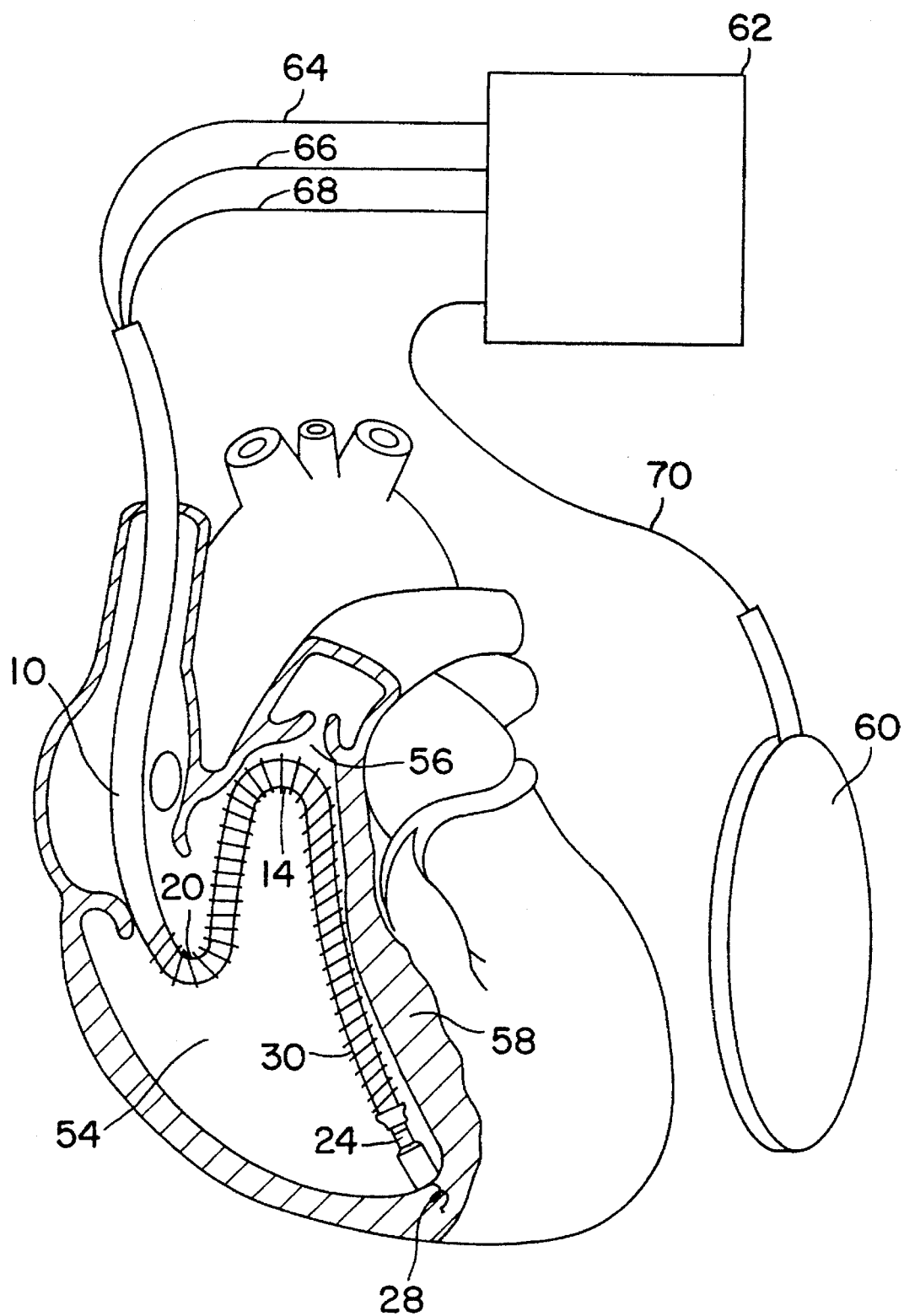
FIG. 2 illustrates the lead of FIG. 1 as implanted in conjunction with a subcutaneous patch electrode.

The outermost of the three conductor coils within sheath 12 is coupled to the proximal end of defibrillation electrode 30, and the middle conductor coil within sheath 12 is coupled to ring electrode 24. As illustrated, insulative sheath 18, around which electrode 30 is mounted, also serves to insulate the outermost conductor coil. The outermost conductor coil may be attached to the proximal end of defibrillation electrode 30 or to both ends of defibrillation coil 30. In the latter case, the outermost conductor coil extends within the insulative sheath 18. The innermost coil is mounted rotatably within an insulative sheath separating the innermost coil from the middle coil, and is mechanically and electrically coupled to helix electrode 28, which is retractably mounted within electrode head 26. Rotation of the innermost conductor coil in one direction causes rotation of electrode 28 and advancement of electrode 28 out the distal end of electrode head 26. Helical pace/sense electrode 28 may be screwed into the tissue of the right ventricle of the heart, and is used to anchor the lead as shown in FIG. 2. The electrode head 26, electrode 28, and the innermost conductor coil employed to rotate the helical electrode 28 are described in more detail in U.S. Pat. No. 4,106,512, to Bisping, incorporated herein by reference in its entirety.

Defibrillation electrode 30 may be mounted around insulative sheath 18 and bonded to sheath 18 by means of a backfill of insulative plastic, as described in the above-referenced '049 patent, incorporated herein by reference in its entirety. As an alternative, the insulative sheath 18 may be fabricated of a polyurethane or other heat flowable material, expanded against the exterior of the electrode coil turns under pressure and heated to allow the material of the sheath to flow between the electrode coil turns, as illustrated in the above-referenced '143 patent by Holleman et al., also incorporated herein by reference in its entirety. Alternatively, the electrode coils may be fabricated using the techniques illustrated in the above-referenced '952 and '953 patents. Defibrillation electrode 30 is preferably made of coiled platinum wire. However, as discussed in the references cited above, other implantable metals have been disclosed for use in such exposed coil, defibrillation electrodes.

In use, the distal section of the lead 10, along which defibrillation electrode 30 partially extends, is located in the right ventricular apex, and is maintained in that position by means of a helical electrode 28. The first loop portion 14, along which electrode 30 extends, is located in the outflow tract of the right ventricle. It is maintained in its location by virtue of its attachment at its proximal end to the main lead body, by the affixation of the distal end of the lead body in the right ventricular apex and by the Ω-shaped curved configuration of the intermediate section.

The Ω-shaped curved configuration illustrated in FIGS. 1 and 2 is maintained by any of a number of known mechanisms. It may be maintained by means of molding insulative sheaths 20 and 18 in the form of a curved tube, or otherwise imparting a predetermined curve to the sheath. For example, the techniques illustrated in U.S. Pat. No. 3,729,008, issued to Berkovits, also incorporated herein by reference in its entirety, to retain the curvature of an atrial J-shape after a straightening stylet may be adapted to the Ω-shape of the present invention.

Alteratively, the electrode coil 30 may be preformed to exhibit the Ω-shaped curved configuration or the conductor coils located within insulative sheath 18 may be preformed to assume the curved configuration. An additional preformed curved coil devoted particularly to maintaining the curved configuration of the lead may also be used, as disclosed in U.S. Pat. No. 4,402,330, to Lindemans, also incorporated herein by reference in its entirety, may also be used to maintain the Ω-shaped curved configuration.

FIG. 1 also illustrates the proximal, connector end of the lead. In this view, it can be seen that electrode connector assembly 36 is attached to the outer sheath 12. Electrode connector assembly 36 is a tripolar connector conforming to the international connector standard designated "IS-1". The standard connector includes ring-shaped connector surfaces 42 and 50 and a hollow lumen, rotatable connector pin 44. Insulative segments 46 and 47, which are each provided with a plurality of sealing rings for sealing the connector within the connector block of an associated implantable defibrillator, separate connector surfaces 42 and 50 and connector pin 44.

The innermost coiled conductor within sheaths 12 and 18 is mechanically and electrically coupled to rotatable pin 44 such that rotation of pin 44 causes rotation of helical electrode 28 into or out of the distal end of electrode head 26. Ring connector 42 is coupled to the middle coiled conductor within sheath 12 attached to pace/sense electrode 24, and is rotationally fixed. The outermost conductor within sheath 12, attached to defibrillation electrode 30, is coupled to connector surface 50 having a somewhat larger diameter than that of connector surface 42. An appropriate structure for producing this IS-1 compatible, rotatable connector pin assembly illustrated may be found in U.S. Pat. No. 4,951,687 issued to Ufford et al., incorporated herein by reference in its entirety.

Connector pin 44 includes an axial lumen permitting passage of a wire styler 52 down the innermost conductive coil lumen located within insulative sheath 12, and to the distal end thereof. Passage of the styler 52 through the lumen of the lead 10 assists in guiding it to its appropriate location in the ventricle, and maintaining it in position while connector pin 44 is rotated to advance helical electrode 28 into the right ventricular apex tissue. Insertion of the stylet 52 into the Ω-shaped curved section of the lead allows for straightening of the Ω-shaped intermediate configuration exhibited by electrode 30, facilitating passage of the lead 10 through the venous system and the tricuspid valve, into the right ventricle 54. After the distal end of the lead is anchored by means of electrode 28, the stylet 52 may be removed from the lumen of the lead, allowing first loop portion 14 to locate itself in the outflow tract of the right ventricle.

FIG. 2 illustrates the lead 10 shown in FIG. 1 as implanted in the right ventricle 54 of the heart with the first loop portion 14 extending into the outflow tract 56. FIG. 2 also illustrates schematically the interconnection of the electrode 30 on the lead 10 and an accompanying subcutaneous electrode 60 with the defibrillator or pacemaker/cardioverter/defibrillator 62. Subcutaneous electrode 60 may be a patch electrode, e.g. that illustrated in U.S. Pat. No. 5,044,374 to Lindemans et al. Preferably, subcutaneous electrode 60 comprises the can of the defibrillator or pacemaker/cardioverter/defibrillator 62. Alternatively, or in addition, a CS electrode may also be employed in the lead and electrode system.

The location of the subcutaneous electrode 60 will vary from patient to patient, depending upon the particular geometry of the patient's heart, and other considerations of bodily structure. However, generally, it can be stated that it would be desirable that the location of the subcutaneous electrode place the majority of the left ventricle mass in the electrical field established by the electrode surfaces of the right ventricular lead and the subcutaneous electrode. These considerations will greatly dictate a subcutaneous electrode location on the left side of the thorax, at or somewhat below the level of the left ventricle.

As illustrated, it can be seen that the proximal end of the electrode 30 is located approximately adjacent the tricuspid valve. However, this point may vary in hearts of differing sizes, and in some cases, it may be desirable to extend the electrode 30 up into the right atrium of the heart. The Ω-shaped curved configuration provides for the orientation of the defibrillation electrode along one of the two generally straight leg portions of the Ω-shaped section of the lead body against the septum 58 dividing the right ventricular chamber 54 from the left ventricular chamber.

In use, a cardioversion or defibrillation pulse is delivered between the electrode 30 and a subcutaneous electrode or an epicardial electrode 60. The implantable pacemaker/cardioverter/defibrillator 62 may be used to deliver such a pulse. A specific example of a defibrillation pulse generator which may be used in conjunction with the present lead is disclosed in U.S. Pat. No. 4,953,551, issued to Mehra et al., incorporated herein by reference in its entirety.

As illustrated schematically, conductors 64 and 66 are coupled to pace/sense electrodes 24 and 28, respectively. Pacemaker/cardioverter/defibrillator 62 monitors heart activity and delivers cardiac pacing pulses via conductors 64 and 66 and cardioversion/defibrillation pulses via conductors 68 and 70 to defibrillation electrodes 30 and 60, respectively.

Figure 3:
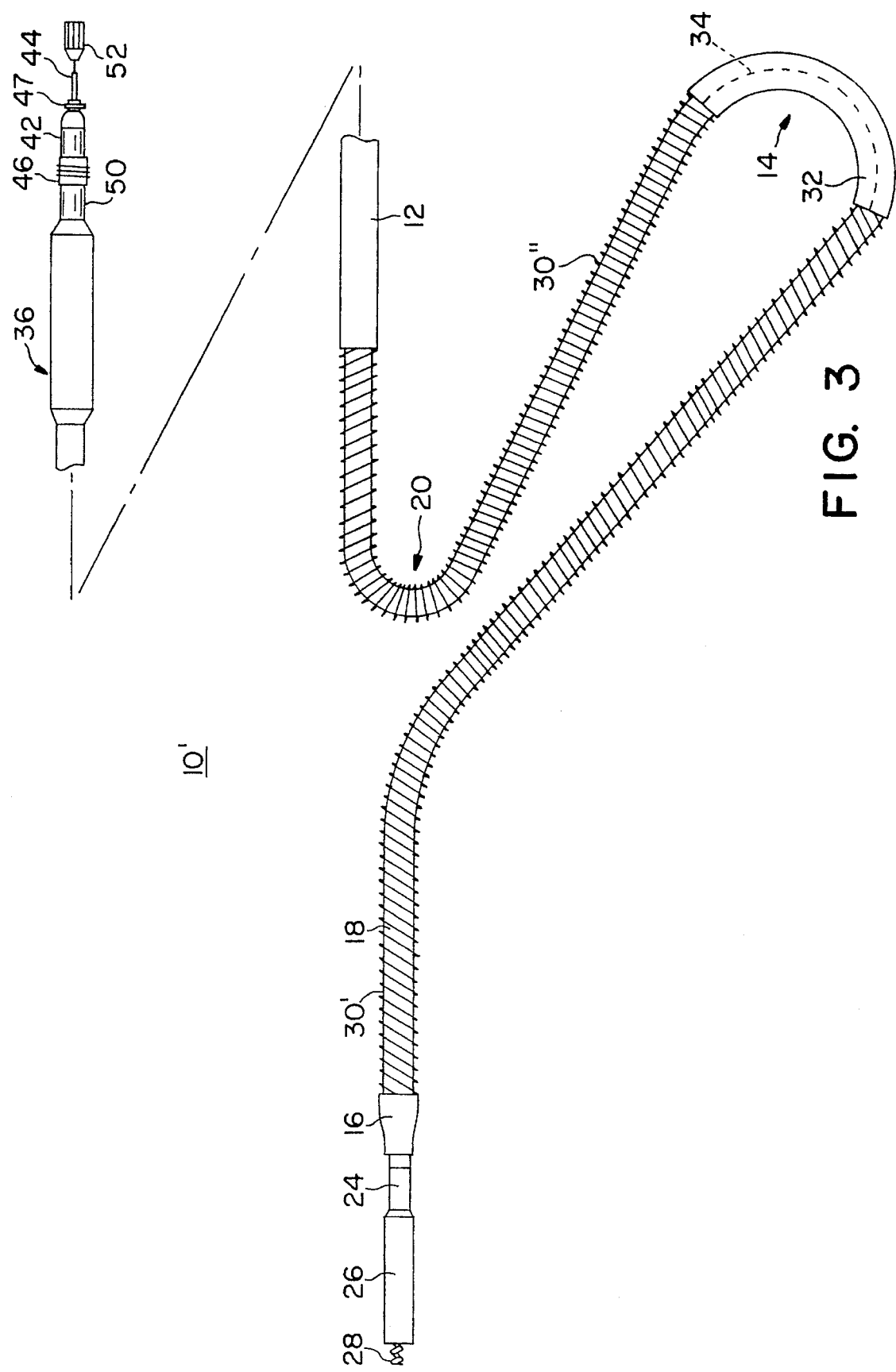
FIG. 3 is a plan view of a further embodiment of the Ω-shaped, RV defibrillation lead according to the present invention implantable as shown in FIG. 2.

FIG. 3 illustrates a modification of the lead 10 of FIG. 1 that may be implanted in the system of FIG. 2 in the same manner as described above. The modified lead 10' of FIG. 3, comprises two (or more) exposed, coiled wire, defibrillation electrode sections 30', 30", for example, separated by the first loop portion 14. The first loop portion 14 is insulated in this case by the outer insulation layer or tubing 32 similar to sheath 12. It will be understood that the electrode sections 30', 30" are electrically connected in series in a manner described, for example, in the above-referenced '288 patent, incorporated herein by reference in its entirety, and as shown schematically by the electrical connection 34.

It will also be understood that the lengths of the exposed coil defibrillation electrode 30 and electrode sections 30', 30" etc. along the leads 10, 10' may be varied. For example, the electrode section 30' may be shortened so that it commences distally of second loop portion 20.

In addition, the pace/sense electrode pair located at the distal end of the second leg portion of the leads 10, 10' may be in some cases be omitted. Similarly, the use of an active fixation device to anchor the distal section of the lead may be omitted, and passive fixation means such as tines or other similar fixation mechanism may be employed instead. Additional electrodes may also be added to the lead body, for example in the portion of the lead which passes through the right atrium.

The defibrillation leads of the present invention advantageously do not include any side branches or bifurcations requiring special installation techniques. The pace/sense electrode pair can advantageously be lodged in the typical deep right ventricular apex position using ordinary endocardial lead implantation techniques.

While a particular stylet mechanism is disclosed for straightening the curved proximal and distal loops of the lead, other mechanisms, e.g. a memory metal coiled loop or a separate introduction catheter may be employed to accomplish this function.

While there has been shown what are considered to be the preferred embodiments of the invention, it will be manifest that many changes and modifications may be made therein without departing from the essential spirit of the invention. The disclosed lead configurations should be considered exemplary, rather than limiting with regard to the interpretation of the following claims. It is intended, therefore, in the following claims to cover all such changes and modifications as may fall within the true scope of the invention.

In conjunction with the above specification, I claim:

1. A cardioversion/defibrillation lead for location in a human heart, comprising:

an elongated lead body having a proximal section extending distally from a proximal end of said lead body and a distal section extending proximally from a distal end of said lead body and having an intermediate section including a first loop portion and two leg portions, a first of said leg portions extending from a second loop portion located at a distal end of said proximal lead section, toward said proximal end of said lead body and ending at said first loop portion, a second of said leg portions extending distally from said first loop portion toward the distal end of said lead body;

means for introducing said intermediate section and said distal section into the right ventricle of the heart with said distal section directed into the apex of the right ventricle of the heart and for locating said first loop portion in the outflow tract of the heart to urge one of said leg portions against the septum of the heart between the outflow tract and the apex;

an elongated defibrillation electrode extending along at least said first and second leg portions;

a conductor located within said lead body, coupled to said defibrillation electrode and extending to said proximal section of said lead body; and connector means coupled to said proximal section of said lead body for electrically coupling said conductor to an implantable defibrillator.

2. A lead according to claim 1 further comprising means for fixing the distal end section of said lead in the apex of the right ventricle of said heart.

3. A lead according to claim 2 wherein said fixing means comprises a fixation helix extending from the distal section of said lead body.

4. A lead according to claim 3 wherein said fixation helix is a helical pace/sense electrode and wherein said lead further comprises a further conductor coupled to said helical pace/sense electrode.

5. A lead according to claim 1 wherein said introducing means comprises means for straightening said intermediate section to effect transvenous introduction of said lead into the patient's heart.

6. A lead according to claim 5 wherein said straightening means comprises a lumen extending the length of the lead and a stiffening stylet which is received in the lumen and straightens said intermediate section of said lead body upon insertion therein.

7. A lead according to claim 1 wherein said elongated defibrillation electrode extends along said first and second leg portions from a proximal electrode end adjacent a proximal end of said first leg portion to a distal electrode end adjacent the distal end section of said lead body.

8. A lead according to claim 7 wherein said electrode extends proximal to said first leg portion.

9. A lead according to claim 1 wherein said elongated defibrillation electrode further comprises:

a proximal electrode section extending from a first point adjacent a proximal end of said first leg portion to said first loop portion;

a distal electrode section extending distally from said first loop portion; and means for electrically connecting said proximal and distal electrode sections to said conductor.

10. A lead according to claim 9 wherein said proximal electrode section extends proximal to said first leg portion.

11. A lead according to claim 1 wherein said first and second loop portions are generally coplanar.

12. A method of locating a cardioversion/defibrillation lead in a heart, comprising:

advancing into the heart an elongated lead body having a proximal section extending distally from a proximal end of said lead body and a distal section extending proximally from a distal end of said lead body and having an intermediate section carrying an elongated electrode and including a first loop portion and two leg portions, a first of said leg portions extending from a second loop section at a distal end of said proximal lead section, toward said proximal end of said lead body and ending at said first loop portion, a second of said leg portions extending distally from said first loop portion back toward the distal end of said lead body;

introducing said intermediate section and said distal section into the right ventricle of the heart with said distal end section directed into the apex of the right ventricle of the heart and locating said first loop portion in the outflow tract of the heart to urge one of said leg portions against the septum of the heart between the outflow tract and the apex.

13. A method according to claim 12 further comprising the step of affixing the distal end of said lead body in the right ventricular apex of said heart.

14. A method according to claim 12 wherein said advancing step comprises straightening said intermediate section to effect transvenous introduction of said lead into the patient's heart.

15. A method according to claim 14 wherein said straightening step comprises inserting a stiffening stylet which is in said lead body.

16. A method according to claim 15 wherein said locating step comprises removing said stiffening stylet from said lead body.

\* \* \* \* \*